United States Patent
Van Wyk et al.

(10) Patent No.: US 7,789,836 B2
(45) Date of Patent: Sep. 7, 2010

(54) SYSTEM, METHOD, AND KIT FOR POSITIONING A MONITOR TRANSDUCER ON A PATIENT

(76) Inventors: Rachelle R. Van Wyk, 10801 Starkey Rd., #104-16, Largo, FL (US) 33777; Robert A. Van Wyk, 10801 Starkey Rd., #104-16, Largo, FL (US) 33777

( * ) Notice: Subject to any disclaimer, the term of this patent is extended or adjusted under 35 U.S.C. 154(b) by 1019 days.

(21) Appl. No.: 11/432,351

(22) Filed: May 12, 2006

(65) Prior Publication Data

US 2007/0167753 A1 Jul. 19, 2007

Related U.S. Application Data

(60) Provisional application No. 60/682,298, filed on May 18, 2005.

(51) Int. Cl.
*A61B 8/00* (2006.01)
(52) U.S. Cl. .................. 600/459; 600/304; 600/453; 600/588
(58) Field of Classification Search .......... 128/870, 128/876; 600/300, 304, 407, 437, 453, 454, 600/456, 586, 588, 459; 607/902
See application file for complete search history.

(56) References Cited

U.S. PATENT DOCUMENTS

| 2,541,487 | A |   | 2/1951  | Triplett |       |
|-----------|---|---|---------|----------|-------|
| 2,923,664 | A |   | 2/1960  | Cook et al. | |
| 3,400,710 | A |   | 9/1968  | Goldstein | |
| 3,561,436 | A |   | 2/1971  | Gaylord et al. | |
| 4,680,205 | A |   | 7/1987  | Lerner et al. | |
| 4,732,146 | A |   | 3/1988  | Fasline et al. | |
| 4,781,200 | A |   | 11/1988 | Baker | |
| 4,825,866 | A |   | 5/1989  | Pierce | |
| 4,949,730 | A | * | 8/1990  | Cobben et al. | 600/588 |
| 5,234,462 | A |   | 8/1993  | Pavletic | |
| 5,437,623 | A |   | 8/1995  | McClees et al. | |
| 5,807,271 | A |   | 9/1998  | Tayebi et al. | |
| 5,843,025 | A |   | 12/1998 | Shaari | |
| 5,871,499 | A | * | 2/1999  | Hahn et al. | 606/202 |
| 6,383,143 | B1 |  | 5/2002  | Rost | |
| 6,570,051 | B1 |  | 5/2003  | Beaudry | |
| 2003/0095150 | A1 | * | 5/2003 | Trevino et al. | 345/810 |
| 2003/0187370 | A1 | * | 10/2003 | Kodama | 600/591 |
| 2005/0033209 | A1 |   | 2/2005 | Rolnick et al. | |

* cited by examiner

*Primary Examiner*—Ruth S Smith
*Assistant Examiner*—Rochelle Reardon
(74) *Attorney, Agent, or Firm*—Chalin A. Smith; Smith Patent Consulting, LLC

(57) ABSTRACT

An improved patient monitoring system is described herein. In particular, the present invention provides an improved system, method, and kit for positioning and removably mounting, often repeatedly, a monitor transducer on a patient, for example, an external fetal monitor used during pregnancy and childbirth labor. The improved system of the present invention avoids many of the disadvantages of conventional monitoring systems in that it maintains transducer position during patient movement, allows the position of the transducer to be changed without repositioning the patient, allows for simple and expeditious adjustment so as to maximize signal quality without causing patient discomfort, eliminates the need for a belt circumferentially disposed about the patient's abdomen, and can be applied to a wide array of body types, including patients having round abdomens. The system, method, and kit of the present invention is not only both efficient and effective but also economical.

19 Claims, 8 Drawing Sheets

SYSTEM, METHOD, AND KIT FOR POSITIONING A MONITOR TRANSDUCER ON A PATIENT

PRIORITY

This application claims the benefit of provisional application 60/682,298 filed May 18, 2005, the contents of which are hereby incorporated by reference in its entirety.

TECHNICAL FIELD OF THE INVENTION

The present invention relates to an improved patient monitoring system and method. More particularly, the present invention relates to a system, method and kit for positioning and removably mounting one or more monitor transducers on a patient, for example, an external fetal monitor system used during pregnancy and childbirth labor.

BACKGROUND OF THE INVENTION

Fetal monitoring is a valuable tool for monitoring and assessing fetal status and labor progress during pregnancy and childbirth. While there are various types of monitors, all monitor the same signals and assess fetal well-being by measuring parameters such as fetal heart rate and observing the effect of maternal influences, such as labor contractions, on the baby's heart rate. In the modern hospital environment of today, monitoring is most often done electronically.

There are two types of electronic monitoring methods: internal and external. Internal monitoring involves affixing a transducer to the baby's scalp to monitor heart rate, and an intrauterine pressure catheter to monitor contractions. Internal monitoring can only be used after the cervix is dilated at least two centimeters. Because of this, internal monitoring cannot be used during preterm or early labor and is generally used only after signs of fetal distress are observed through an external monitoring method.

The conventional external electronic fetal monitor is a two-belt ultrasound device that is strapped about the mother's abdomen. One belt holds a listening device (e.g., an acoustic signal transducer) in place while the other belt holds the contraction monitor (e.g., a pressure signal transducer). The nurse or midwife frequently must adjust the belts to get the best readings from each device. The response of the baby's heartbeat to uterine contractions is used to determine the baby's health and well-being. For example, a deceleration or drop in fetal heart rate following a contraction may indicate that the baby is not getting enough oxygen, an early sign of possible fetal distress. One or both of the transducers may be used intermittently or continuously during labor. Frequently the transducers are used intermittently during early labor and continuously during later stages of labor. In addition, mothers hospitalized for preterm labor and pregnancy complications often must wear the external fetal monitor continuously for extended periods.

The present method for external fetal monitoring, using circumferential belts to position the heart rate and uterine contraction transducers, has several distinct disadvantages. For example, the belts limit the mobility of the mother since movement by the mother frequently causes the positions of the belts and transducers to shift, thereby causing the loss of one or both of the signals. The loss of the fetal heartbeat signal due to movement of the transducer may cause an alarm on the monitor to sound requiring the attention of a clinician and causing anxiety to the mother. Often the mother must remain relatively motionless, in a more or less prone position, a circumstance that both increases patient discomfort and slows the progress of labor. Each time a transducer is dislodged by patient movement, a nurse or other clinician must hunt around with the transducer to find a "sweet spot" in which a clear signal is obtained and adjust the associated belt to keep the transducer in this position. This happens frequently during labor. Also, as the baby often changes position, the transducer location must also be changed to obtain a suitable signal. This repositioning of the transducer requires an associated repositioning of the appropriate belt, an operation which frequently causes discomfort for the mother.

If the monitor is being used intermittently, it is necessary to apply and remove the associated belts from the mother, again causing discomfort. In addition, some patients have a shape which does not allow transducers to be reliably positioned on their abdominal region using the current belt system. Accordingly, there is a need for an improved system and method for positioning and retaining monitoring transducers on a patient. The present invention addresses that need.

SUMMARY OF THE INVENTION

It is an object of the present invention to provide a system, method, and kit for positioning and removably mounting a monitor transducer on a patient.

It is a further object of the present invention to provide a system, method, and kit wherein the transducer position is maintained during patient movement.

It is a further object of the present invention to provide a system, method, and kit that allows the position of the transducer to be changed without repositioning the patient.

It is a further object of the present invention to provide a system, method, and kit that allows for simple and expeditious adjustment so as to maximize signal quality without causing patient discomfort.

It is a further object of the present invention to provide a system, method, and kit that eliminates the need for a belt circumferentially disposed about the patient's abdomen.

It is a further object of the present invention to provide a system, method, and kit that can be applied to a wide array of body types, including patients having round abdomens.

It is a further object of the present invention to provide a system, method, and kit that is both efficient and effective yet also economical.

Accordingly, the present invention provides an external fetal monitoring system comprising:
  (a) two or more anchor strips, each of which include a layer of adhesive material disposed on one side and one or more fasteners disposed on the opposite side;
  (b) one or more elastomeric straps, each of which include one or more fastener receivers disposed at either end, wherein the fasteners and fastener receivers mate to form a fastener pair; and
  (c) one or more monitor transducers, each of which include retaining features on one side thereof, the retaining features allowing said one or more transducers to be affixed to said one or more elastomeric straps.

In one embodiment, transducer(s) are slidably affixed to the elastomeric strap(s). Alternatively, each transducer may be held in place by first and second strap "halves" or "portions", wherein one end of a strap portion is attached to the transducer and the other end is attached to the anchor strip.

In a preferred embodiment, the transducers include a pressure signal transducer and an acoustic signal transducer, such as a sonic or ultrasonic transducer.

In a further preferred embodiment, the fastener pair is selected from mating hook and loop fabric, hooks and eyes, buttons and button holes, and snaps.

The present invention further provides a method for positioning at least one monitor transducer on a patient by means of the above described system. In a preferred embodiment, the method comprises the steps of:

(a) attaching the two or more anchor strips in a more or less vertical and laterally spaced fashion to a patient's abdomen;
(b) mounting the one or more monitor transducers to the one or more elastomeric straps;
(c) extending the one or more elastomeric straps in a relatively horizontal fashion across the patient's abdomen and attaching either end of the straps to the anchor strips by means of the mating fasteners and fastener receivers; and
(d) positioning the one or more transducers so that it measures a desired parameter.

In a further preferred embodiment, the desired parameters to be measured include fetal heartbeat and intrauterine contraction frequency, strength and duration.

The present invention further provides a kit for external fetal monitoring comprising:

(a) one or more pairs of anchor strips, each of which include a layer of adhesive material disposed on one side and one or more fasteners disposed on the opposite side;
(b) one or more elastomeric straps, each of which include one or more fastener receivers disposed at either end, wherein the fasteners and fastener receivers mate to form a fastener pair; and
(c) one or more monitor transducers, each of which include retaining features on one side thereof, the retaining features allowing said one or more transducers to be slidably affixed to said one or more elastomeric straps.

These and other objects and features of the invention will become more fully apparent when the following detailed description is read in conjunction with the accompanying figures and examples. However, it is to be understood that both the foregoing summary of the invention and the following detailed description are of illustrative and preferred embodiments, and are not restrictive of the invention or other alternate embodiments of the invention.

DETAILED DESCRIPTION OF THE PREFERRED EMBODIMENTS

The embodiments described herein are merely intended to illustrate the principles of the invention. Those skilled in the art will recognize that variations and modifications may be made to the embodiments without changing the principles of the invention herein disclosed. Accordingly, the accompanying figures, described in detail below, that depict aspects of the invention are in no way intended to limit the scope of the present invention.

As used herein, the noted directional terms relate to a human body in a standing position. For instance, "up" refers to in the direction of the head, "down" refers to in the direction of the feet. Herein, the "vertical" direction is parallel to the axis of the body and the "horizontal" direction is parallel to the floor. "Lateral" refers to the direction extending away from the center of the body whereas "medial" refers to a direction extending toward the center of the body.

The present invention contemplates the use of one or more "transducers". The transducer may be any device that converts one parameter, such as sound, temperature, pressure, light, or other signals, into an electronic signal. Exemplary transducers include, but are not limited to, piezoelectric crystals, microphones, photoelectric cell, and the like. In the context of external fetal monitoring, a first transducer measures an acoustic signal (e.g., the baby's heartbeat) while a second transducer measures a pressure signal (e.g., an intrauterine contraction). While the preferred embodiments utilize sonic and ultrasonic transducers, other measuring mechanisms are contemplated.

Figure 1:
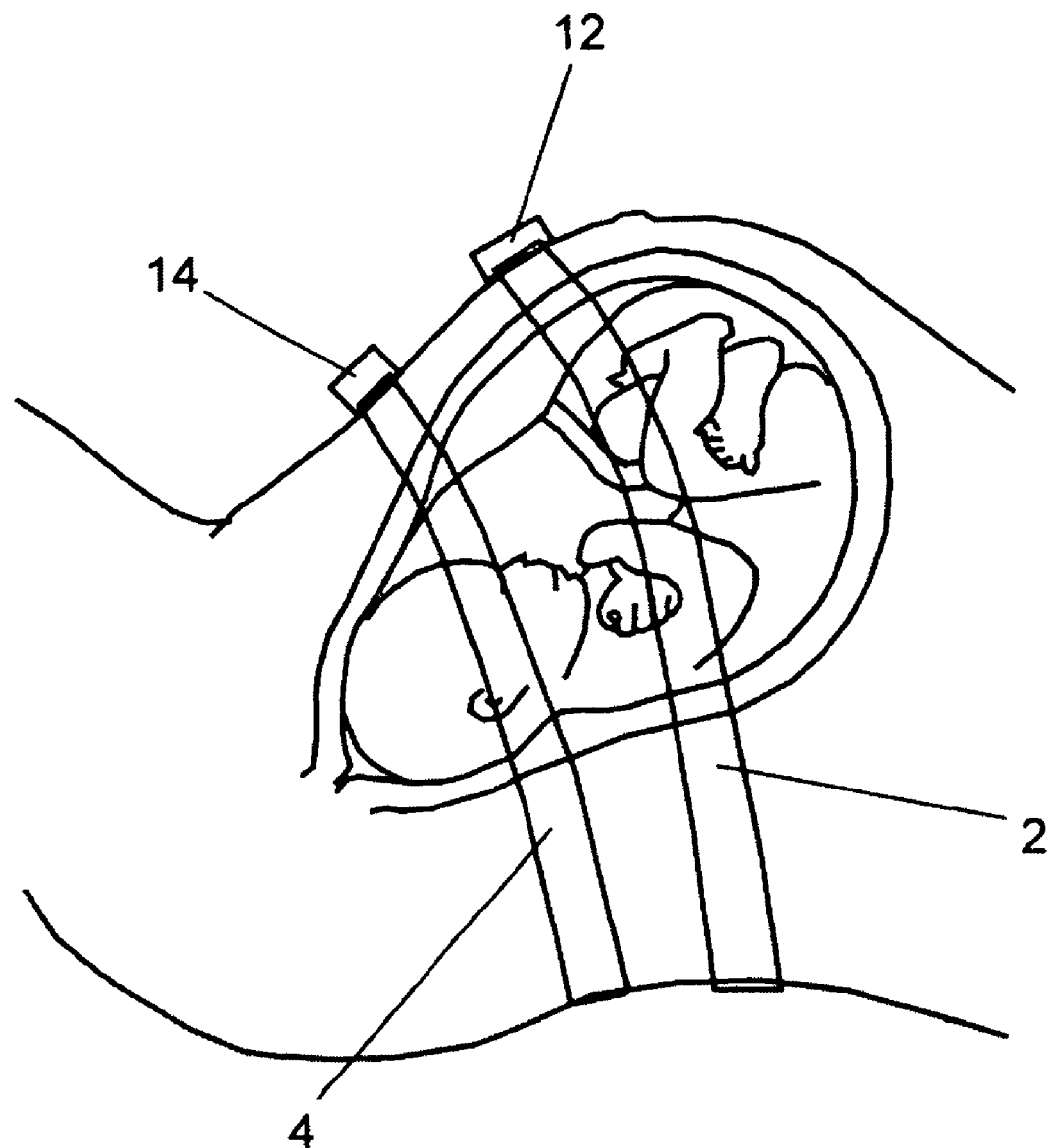
FIG. 1 is a side elevational view of a prior art means for mounting transducers on a pregnant patient during a prenatal diagnostic procedure (e.g., a non-stress test) or during preterm, early or active labor.

Referring now to the figures, FIG. 1 shows a prior art method of positioning and retaining monitoring transducers to the body of a pregnant woman, for example during routine or emergency assessments and childbirth labor. A first transducer 1 is retained on the body of the woman by a first circumferential belt 2. A second transducer 3 is retained on the body of the patient by a second circumferential belt 4. Transducers 1 and 3 are positioned so as to maximize signal strength, the signals being the fetal heartbeat and uterine contractions. Discomfort during pregnancy and labor results in frequent movement of the patient, which, in turn, necessitates frequent repositioning of the belts and/or transducers. Because belts 2 and 4 are circumferential, movement by the patient frequently causes movement of the belts and/or dislodging of the transducers from their positions.

Figure 2:
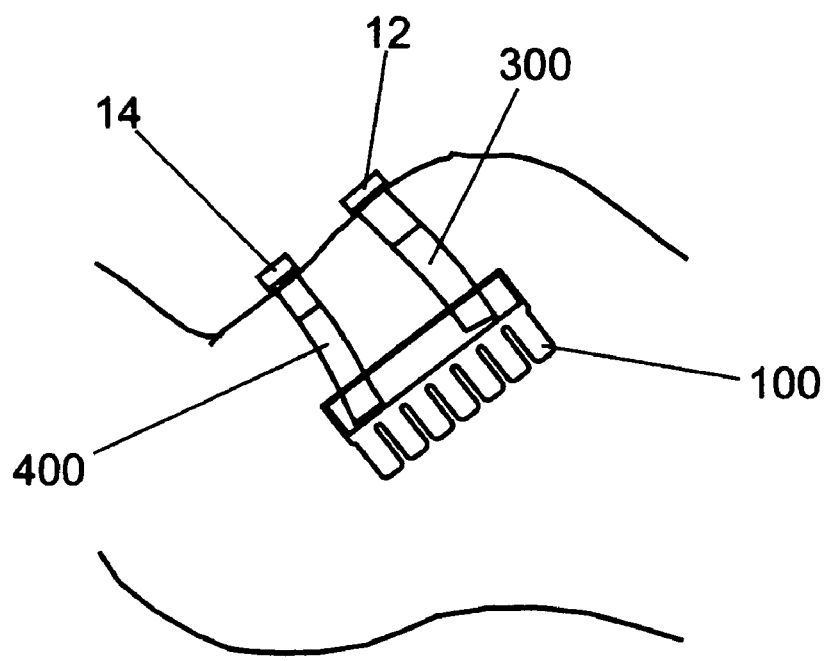
FIG. 2 is a side elevational view of a mounting system constructed in accordance with the principles of this invention for mounting a pair of transducers to a patient's abdomen, for example to a pregnant patient during a prenatal diagnostic procedure or labor.
Figure 3:
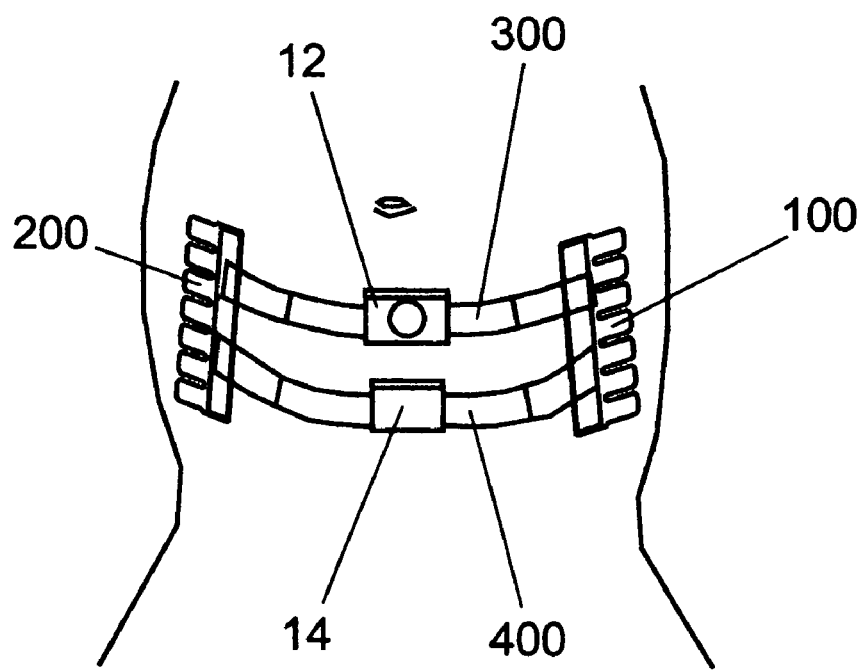
FIG. 3 is a plan view of the objects of FIG. 2.

Referring now to FIGS. 2 and 3 showing a mounting system 10 for transducers constructed in accordance with the principles of this invention, first anchor strip 100 and second anchor strip 200 are positioned more or less vertically on lateral sides of the abdomen, and first transverse strap 300 and second transverse strap 400 extend between anchor strips 100 and 200. First transducer 12 is removably affixed to first lateral strap 300, and second transducer 14 is removably affixed to second lateral strap 400.

Figure 4:
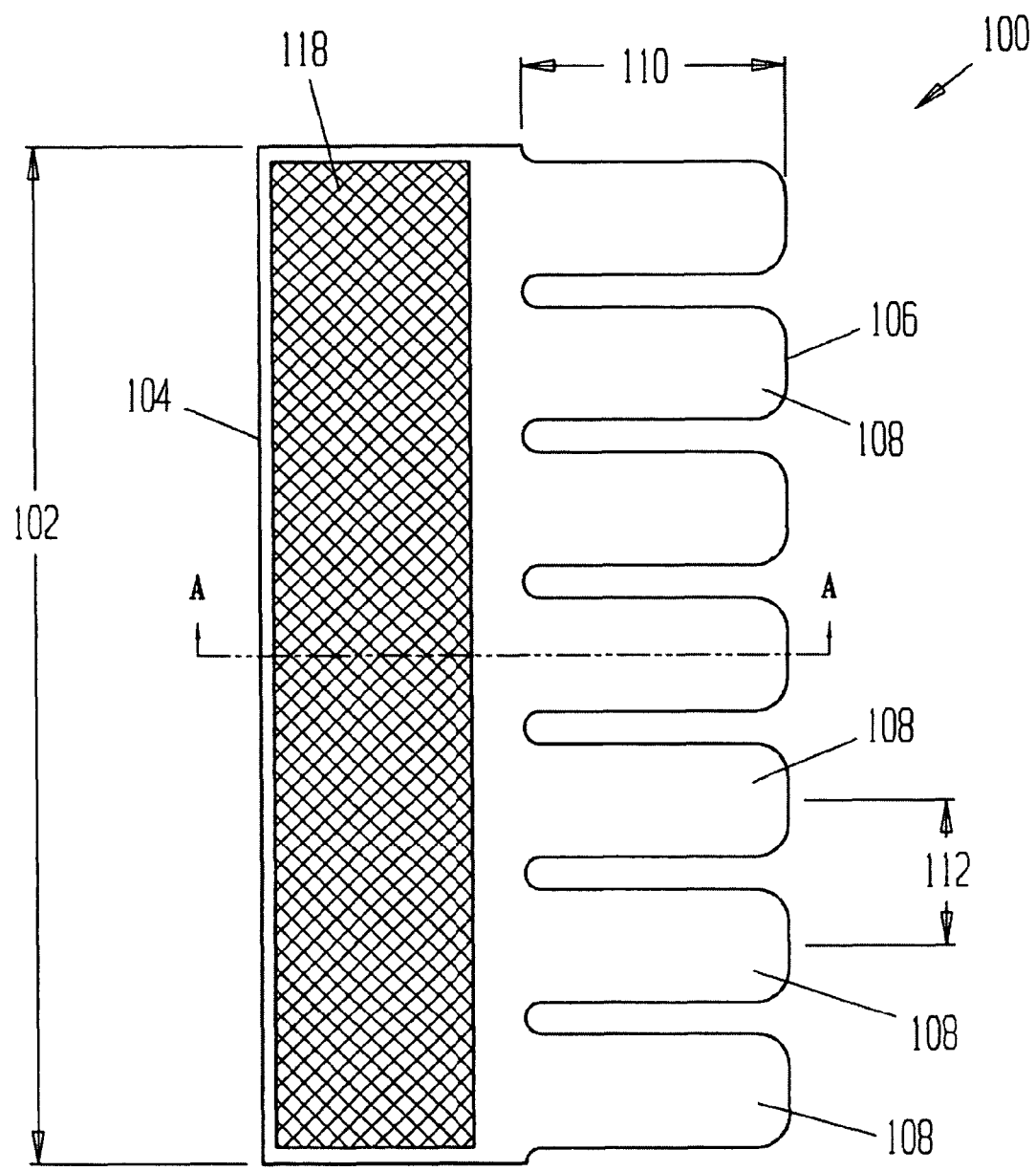
FIG. 4 is a plan view of an anchor strip for use with the system of FIG. 2.
Figure 5:
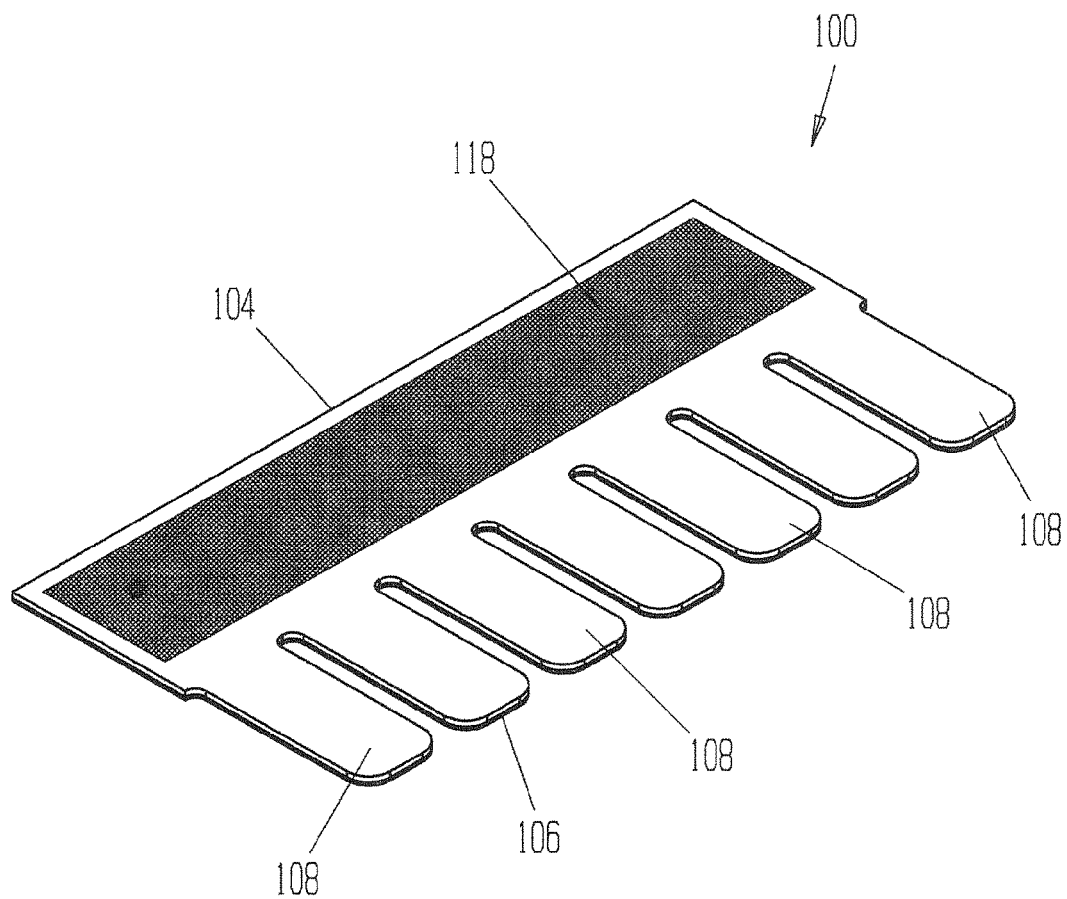
FIG. 5 is a perspective view of the objects of FIG. 4.
Figure 6:
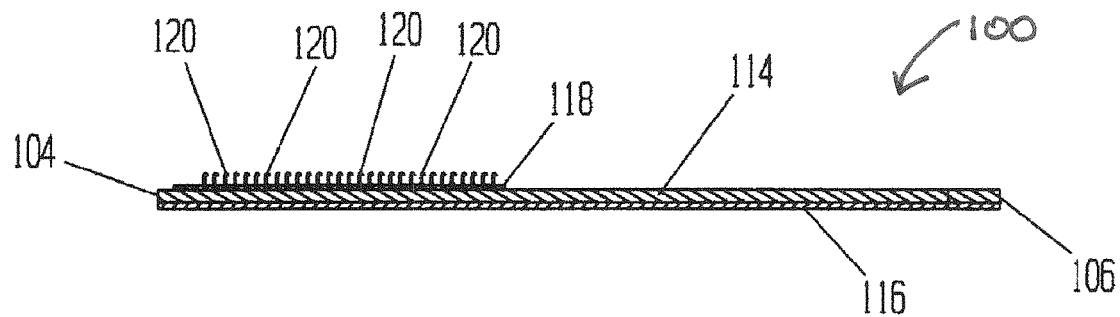
FIG. 6 is a side elevational sectional view of the object of FIG. 4 at location A-A of FIG. 4.

Referring now to FIGS. 4 through 6, anchor strip 100 of length 102 has a medial edge 104 and a lateral edge 106 which forms a plurality of laterally extending, elongated portions (e.g., tabs) 108 of length 110 spaced distance 112 apart. When strip 100 is applied to an abdominal wall, elongated portions 108 wrap adapt to the curvature of the wall laterally so as to provide both increased patient comfort and increased holding strength, particularly when the strip is subjected to a lateral force as frequently occurs during routine use. Length 102 is preferably an integral multiple of distance 112. For instance, if distance 112 is one inch, length 102 is preferably an integral multiple thereof such as, for example, five inches, six inches or seven inches. As best seen in FIG. 6, anchor strip 100 has a first layer 114, formed of a compliant material such as polymeric foam, a second layer 116 formed of an adhesive material suitable for application to the skin in medical applications, and a third layer 118 having a lower surface which is permanently joined to layer 114 and an upper surface having a plurality of hook-shaped protrusions 120 suitable for removably fastening to a pile fabric so as to form a hook and loop fastener pair. Lateral anchor strip 200 is identical in construction to medial anchor strip 100.

Figure 7:
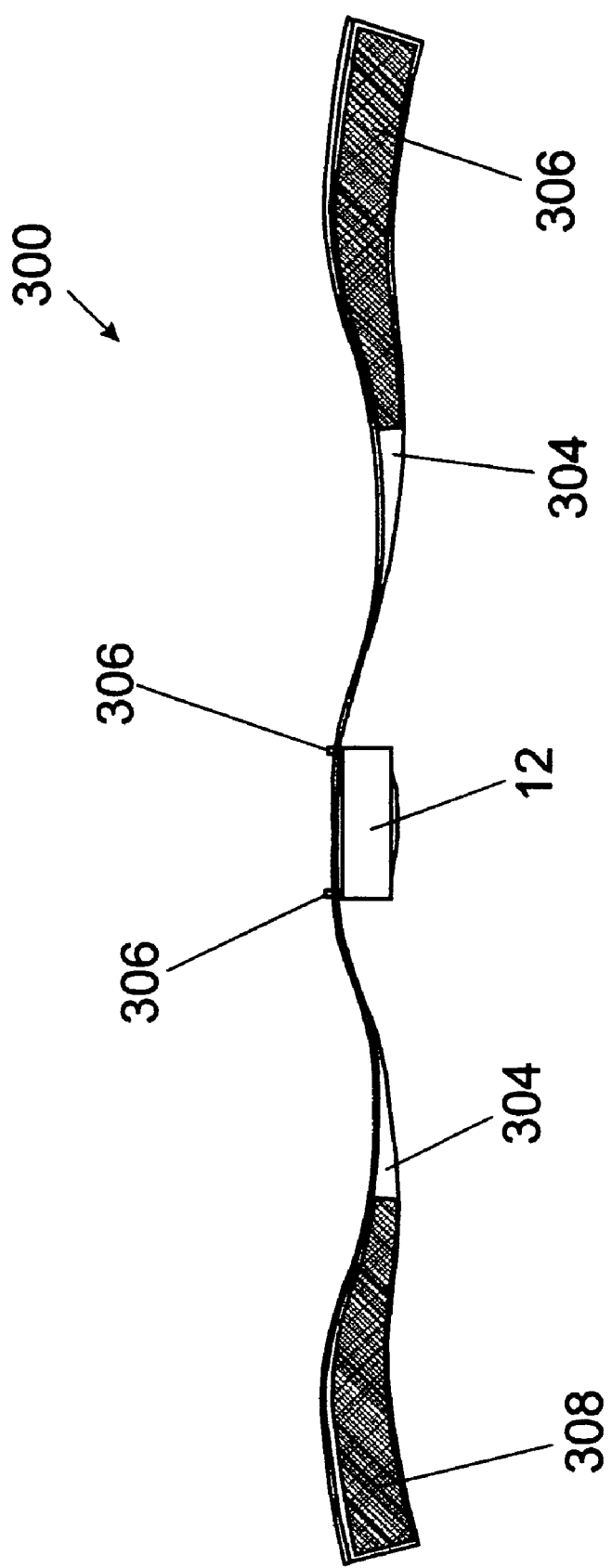
FIG. 7 is a side elevational view of a lateral strap of the system of FIG. 2.

Referring now to FIG. 7, first lateral strap 300 is made from an elastomeric material and has a top surface 302 and a bottom surface 304. Retaining features 306 on the back of first transducer 12 retain the transducer on strap 300 yet allow for slidable movement of the transducer along the length of said strap. Strap 300 has on its bottom surface 304 first region 306 and second region 308 in which a pile material is bonded to surface 304. The pile material is suitable for forming a hook and loop fastener pair with protrusions 120 of layer 118 of anchor strips 100 and 200.

The reverse orientation, wherein the lateral strap is provided with the hook protrusions and the anchor strip is provided with the pile material, is also contemplated. Other fastening means for removably affixing lateral straps 300 and 400 to anchor strips 100 and 200 are also contemplated. For instance, hooks which engage the fabric of the elastomeric strap per se rather than a pile material affixed thereto, may be mounted to the anchor strips or vice versa. Alternatively, such hooks may engage a plurality of eyelets in the fabric of the elastomeric strap. In other embodiments, buttons and/or snaps may be used.

Figure 8A:
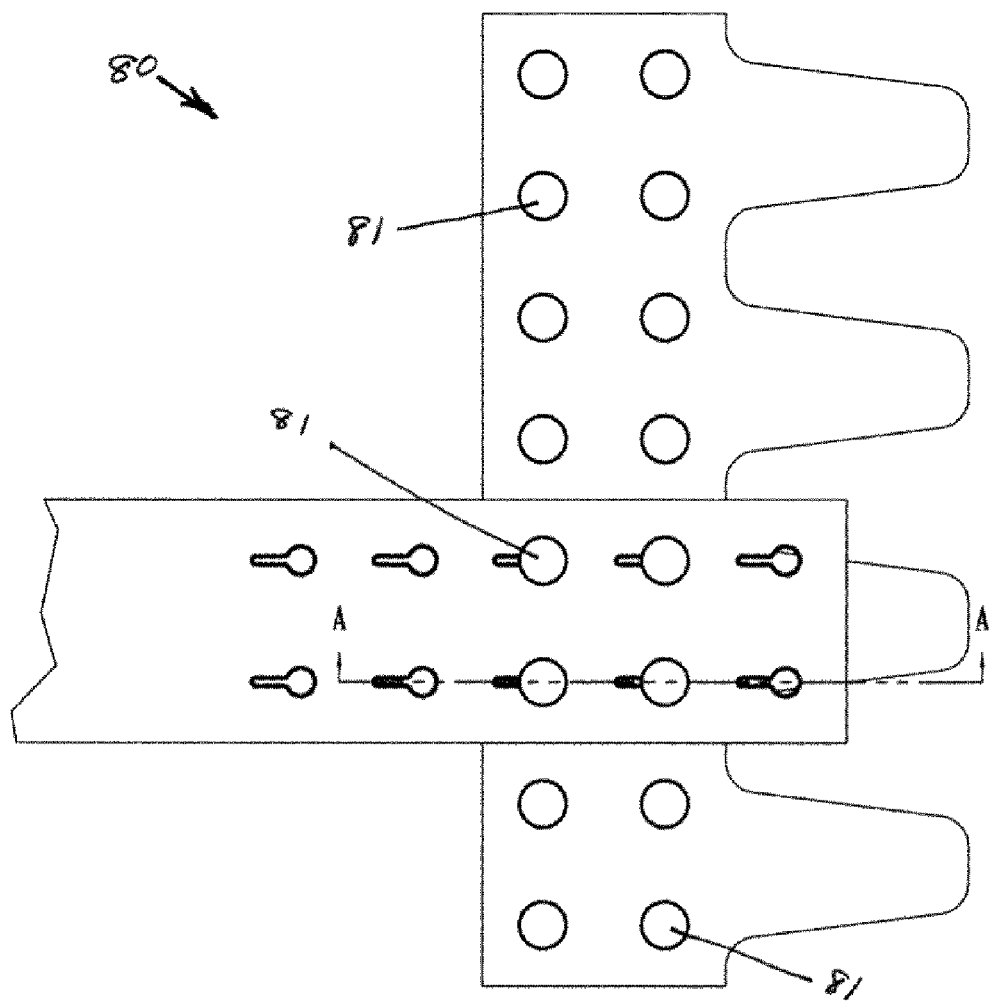
FIG. 8A is a plan view of an anchor strip and elastomeric strap having an alternate fastener combination (i.e., buttons and button holes).
Figure 8B:
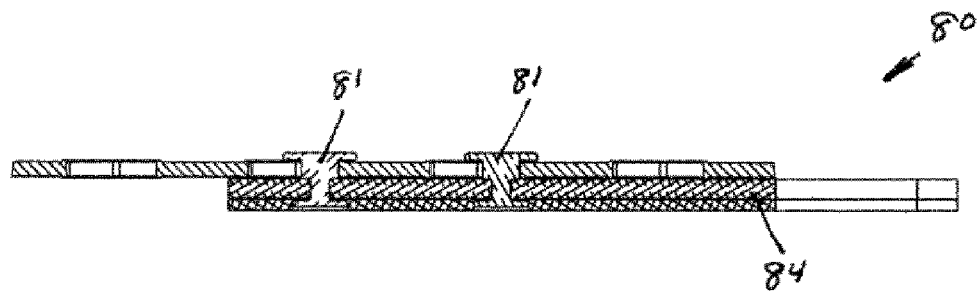
FIG. 8B is a side elevational view of the object of FIG. 8A at location A-A.
Figure 8C:
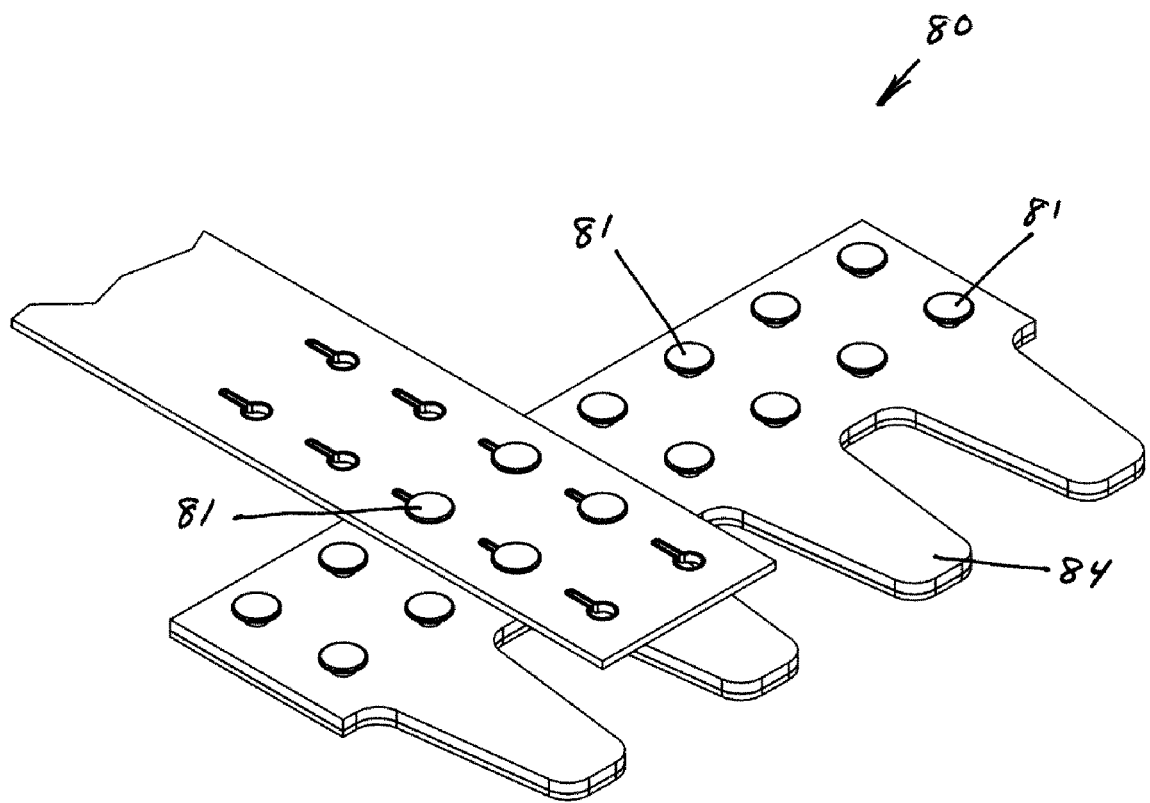
FIG. 8C is a side elevational view of the anchor strip and elastomeric strap embodiment shown in FIG. 8A.

Alternate fastening embodiments are depicted in FIGS. 8 and 9. Referring to FIGS. 8A-8C, anchor strip 80 is designed for use with an elastomeric strap 85 which does not have a pile fabric layer attached. It is identical in configuration and function to the anchor strip 100 of FIG. 5 except that third layer 118 of strip 100 (FIG. 6) with its multiple hooked protrusions, is replaced by one or more buttons 81 attached to second layer 84. Buttons 81 engage button holes 82 disposed in the fabric of the elastomeric strap 85.

Figure 9A:
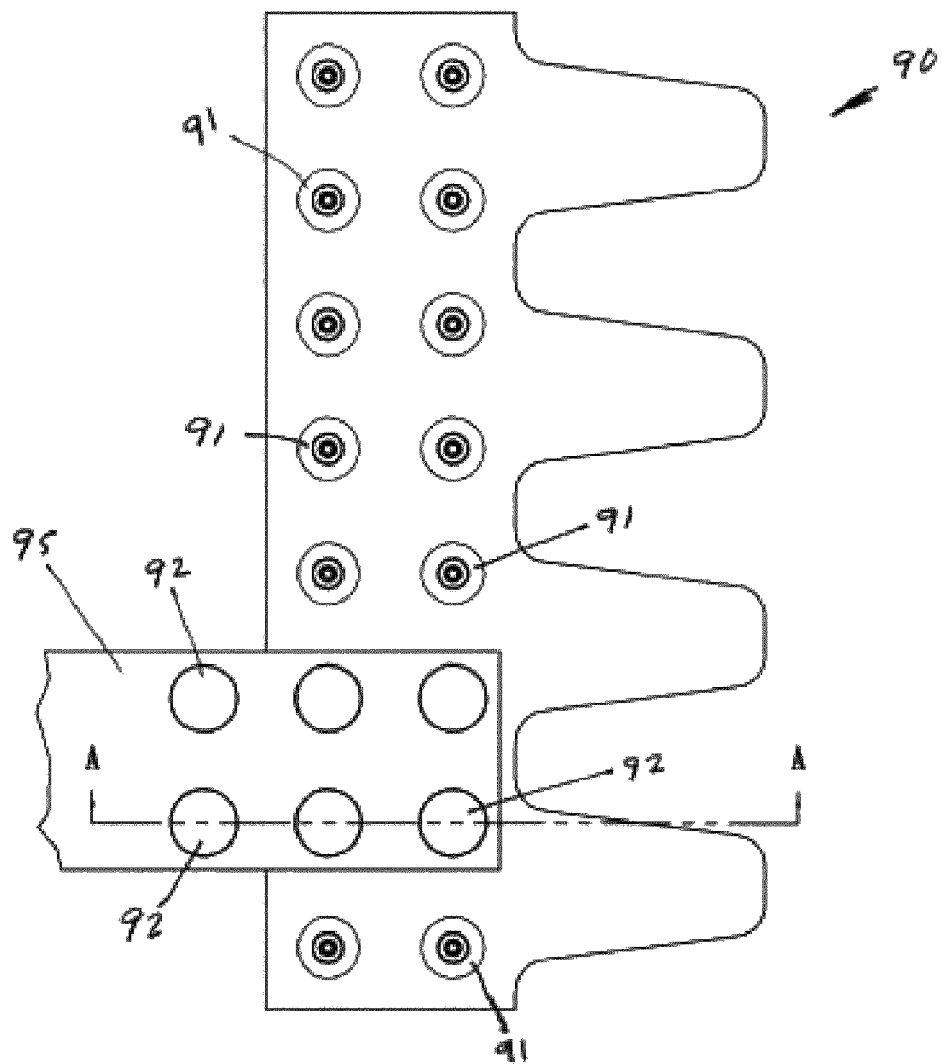
FIG. 9A is a plan view of an anchor strip and elastomeric strap having an alternate fastener combination (i.e., mating snaps).
Figure 9B:
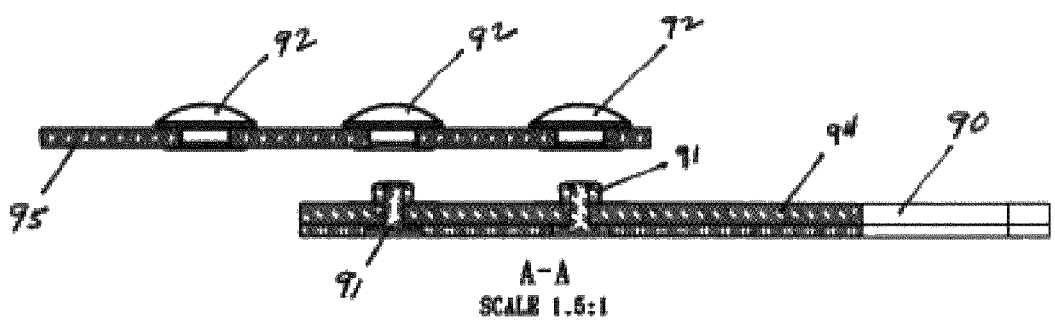
FIG. 9B is a side elevational view of the object of FIG. 9A at location A-A.

Referring to FIGS. 9A-9B, anchor strip 90 is designed for use with an elastomeric strap 95 which does not have a pile fabric layer attached. It is identical in configuration and function to the anchor strip 100 of FIG. 5 except that third layer 118 of strip 100 (FIG. 6) with its multiple hooked protrusions, is replaced by one or more snaps 91 attached to second layer 94. Snaps 91 engage mating snap fasteners 92 disposed in the fabric of the elastomeric strap 95.

In use, first anchor strip 100 and second anchor strip 200 are applied to the abdominal wall, laterally opposed and more or less vertically. First transducer 12 is removably mounted to first lateral strap 300. Transducer 12 is positioned on the abdomen of the patient in a location which gives an acceptable signal to the monitoring system. While maintaining the transducer location, first end 320 of strap 300 is removably affixed to first anchor strip 100, the pile of first region 306 of bottom surface 304 of strip 300 and hooked protrusions 120 of third layer 118 of anchor strip 100 forming a fastener pair. Second end 322 of strap 300 is removably affixed to second anchor strip 200 in the same manner as end 320, an initial tension being applied to strip 200 prior to fastening so as to ensure acceptable compressive force between transducer 12 and the patient's abdominal wall. Second transducer 14 is positioned and retained on the patient in the manner as transducer 12 using second lateral strip 400.

If repositioning of a transducer is required, the ends of the appropriate lateral strap are removed from the anchor strips and the transducer is repositioned and affixed in the manner previously described.

During use, the elastomeric straps can be rapidly adjusted, removed and reapplied as needed. For example, their placement and the amount of initial tension can be adjusted to maximize patient comfort. In addition, one or more of the anchor strips can be removed and reapplied as needed. For example, it may be necessary to replace one or more of the anchor strips, for instance during prolonged labor. In such circumstances, fresh (unused) anchor strips can be applied and the previously used lateral straps and transducers may be mounted in the manner previously described. Another aspect of the present invention is a low-cost kit for mounting transducers to a patient during labor, the kit containing multiple lateral straps and multiple pairs of anchor strip assemblies, all components of the kit being fabricated from economic materials such that they may be discarded after use.

In the embodiment previously herein described, transducers 12 and 14 are slidably positioned on straps 300 and 400 respectively. In other embodiments, strap 300 or strap 400 or both are formed so has to have a first portion and a second portion, each portion having a first end removably attachable to a transducer, and a second end attachable to an anchor strip as previously herein described.

While the present invention is described in terms of two anchor strips, two traverse straps and two transducers, it will be readily apparent to those skilled in the art that multiple strips, straps, and transducers may be combined as needed, particularly when the pregnancy involves multiple fetuses.

The disclosure of each publication, patent or patent application mentioned in this specification is specifically incorporated by reference herein in its entirety.

The invention has been illustrated by reference to specific examples and preferred embodiments. However, it should be understood that the invention is intended not to be limited by the foregoing description, but to be defined by the appended claims and their equivalents.

What is claimed is:

1. An external fetal monitoring system comprising:
    a. two or more discrete anchor strips characterized as having opposed medial and lateral edges and opposed upper and lower surfaces, wherein each of said anchor strips is comprised of (i) a first layer of adhesive material adapted for application to the skin in medical applications and configuring said anchor strip lower surface for attachment to a patient's skin, and (ii) a second layer composed of a compliant material having one or more fasteners disposed thereon and configuring said anchor strip upper surface for attachment to a corresponding fastener receiver, wherein said first and second layers are permanently joined to each other;
    b. one or more discrete elongate elastomeric straps characterized as having opposed first and second ends and opposed upper and lower surfaces, wherein each end of each of said one or more straps has one or more fastener receivers disposed on the lower surface thereof and is configured for removable attachment to the one or more fasteners of said anchor strip second layer, wherein said elastomeric strap fastener receivers and anchor strip fasteners mate to form a fastener pair; and
    c. one or more monitor transducers mounted to said one or more elastomeric straps by a retaining means disposed on one side thereof, said retaining means for laterally moving said one or more monitor transducers along the length of said one or more elastomeric straps so that said one or more transducers can be rapidly repositioned.

2. The system of claim 1, wherein said retaining means comprises one or more members through which at least one of said one or more elastomeric straps is fed, such that said one or more transducers can slide from one end of said one or more elastomeric straps to the other.

3. The system of claim 1, wherein said one or more fasteners comprise a plurality of hook-shaped protrusions and said one or more fastener receivers comprise a plurality of eyes or pile fabric pad.

4. The system of claim 1, wherein said one or more fasteners comprise a plurality of eyes or a pile fabric pad and said one or more fastener receivers comprise a plurality of hook-shaped protrusions.

5. The system of claim 1, wherein at least one of said one or more fasteners comprises a button and at least one of said one or more fastener receivers comprises a button hole.

6. The system of claim 1, wherein said one or more fasteners and said one or more fastener receivers comprise mating snaps.

7. The system of claim 1, wherein each anchor strip's lateral edge comprises a plurality of elongated, laterally extending tabs.

8. The system of claim 1, wherein said compliant material is polymeric foam.

9. The system of claim 1, wherein at least one of said one or more elastomeric straps comprises a fabric belt.

10. The system of claim 1, wherein at least one of said one or more monitor transducers comprises a sonic or ultrasonic transducer.

11. The system of claim 1, wherein at least one of said one or more monitor transducers comprises an acoustic signal transducer and a pressure signal transducer.

12. A method for positioning at least one monitor transducer on a patient comprising the steps of:
   a. providing the external fetal monitoring system of claim 1;
   b. positioning said two or more anchor strips on a patient's abdomen in a substantially vertical and laterally spaced fashion and attaching said strips to said patient's abdomen by means of said first layer adhesive material;
   c. extending said one or more elastomeric straps in a substantially horizontal fashion across the patient's abdomen, transverse to said anchor strips, and attaching the first and second ends of said one or more elastomeric straps to said anchor strips by means of said mating fasteners and fastener receivers; and
   d. positioning said one or more transducers along the length of said one or more elastomeric straps so as to measure a desired parameter.

13. The method of claim 12, further comprising the step of feeding at least one of said one or more elastomeric straps through the retaining means provided on said one or more monitor transducers, to thereby adapt said one or more transducers for sliding from one end said one or more elastomeric straps to the other.

14. The method of claim 12, further including the step of adjusting said one or more transducers without detaching said elastomeric straps from said anchor strips.

15. The method of claim 12, wherein said one or more transducers comprise an acoustic signal monitor and a pressure signal monitor, further wherein step (d) includes the step of measuring fetal heartbeat and intrauterine contractions by means of said acoustic signal monitor and pressure signal monitor.

16. The method of claim 12, wherein step (d) includes the step of measuring fetal heartbeat.

17. The method of claim 12, wherein step (d) includes the step of measuring intrauterine contractions.

18. A kit for external fetal monitoring comprising:
   a. one or more pairs of discrete anchor strips characterized as having opposed medial and lateral edges and opposed upper and lower surfaces, wherein each of said anchor strips is comprised of (i) a first layer of adhesive material adapted for application to the skin in medical applications and configuring said anchor strip lower surface for attachment to a patient's skin, and (ii) a second layer composed of a compliant material having one or more fasteners disposed thereon and configuring said anchor strip upper surface for attachment to a corresponding fastener receiver, wherein said first and second layers are permanently joined to each other;
   b. one or more elastomeric straps characterized as having opposed first and second ends and opposed upper and lower surfaces, wherein each end of each of said one or more straps has one or more fastener receivers disposed on the lower surface thereof and is configured for removable attachment to the one or more fasteners of said anchor strip second layer, wherein said elastomeric strap fastener receivers and anchor strip fasteners receivers mate to form a fastener pair; and
   c. one or more monitor transducers mounted to said one or more elastomeric straps by a retaining means disposed on one side thereof, said retaining means for laterally moving said one or more monitor transducers along the length of said one or more elastomeric straps so that said one or more transducers can be rapidly repositioned.

19. An external fetal monitoring system comprising:
   a. two or more discrete anchor strips characterized as having opposed medial and lateral edges and opposed upper and lower surfaces, wherein each of said anchor strips is comprised of (i) a first layer of adhesive material adapted for application to the skin in medical applications and configuring said lower surface for attachment to a patient's skin and (ii) a second layer composed of a compliant material having one or more fasteners disposed thereon and configuring said anchor strip upper surface for attachment to a corresponding fastener receiver, wherein said first and second layers are permanently joined to each other;
   b. one or more discrete elongate elastomeric straps, each comprised of a first portion and a second portion, wherein each first and second portion is characterized as having opposed first and second ends and opposed upper and lower surfaces wherein (i) the first ends of said first and second portions are adapted for attachment to a transducer and (ii) the second ends of said first and second portions have one or more fastener receivers disposed on the lower surface thereof and are configured for removable attachment to the one or more fasteners of said anchor strip second layer, wherein said elastomeric strap fastener receivers and anchor strip fasteners mate to form a fastener pair; and
   c. one or more monitor transducers, each of which is mounted to said second ends of said first and second elastomeric strap portions by means of one or more retaining means through which said second ends are fed, said retaining means for rapidly repositioning said one or more monitor transducers through adjustment of the relative lengths of said first and second strap portions.

* * * * *